United States Patent [19]
Hollis et al.

[11] Patent Number: 5,371,083
[45] Date of Patent: Dec. 6, 1994

[54] SYNERGISTIC COMBINATIONS OF IONENES WITH HEXAHYDRO-1,3,5-TRIS-(2-HYDROXYETHYL)-S-TRIAZINE IN CONTROLLING FUNGAL AND BACTERIAL GROWTH IN SYNTHETIC METALWORKING FLUIDS

[75] Inventors: C. George Hollis, Memphis; S. Rao Rayudu, Germantown, both of Tenn.

[73] Assignee: Buckman Laboratories International, Inc., Memphis, Tenn.

[21] Appl. No.: 13,237

[22] Filed: Feb. 3, 1993

Related U.S. Application Data

[63] Continuation of Ser. No. 741,986, Aug. 6, 1991, abandoned, which is a continuation of Ser. No. 413,282, Sep. 27, 1989, abandoned.

[51] Int. Cl.⁵ .................... A01N 33/12; A01N 43/66; A61K 31/74
[52] U.S. Cl. .................... 514/241; 424/78.08; 514/642; 514/643
[58] Field of Search .................... 424/78.08; 514/241, 514/642, 643

[56] References Cited

U.S. PATENT DOCUMENTS

| | | | |
|---|---|---|---|
| 3,874,870 | 4/1975 | Green et al. | 71/67 |
| 3,931,319 | 1/1976 | Green et al. | 260/567.6 |
| 4,027,020 | 5/1977 | Green et al. | 526/11.1 |
| 4,089,977 | 5/1978 | Green et al. | 260/567.6 P |
| 4,111,679 | 12/1978 | Shair et al. | 71/67 |
| 4,506,081 | 3/1985 | Fenyes et al. | 548/523 |
| 4,581,058 | 4/1986 | Fenyes et al. | 71/67 |

FOREIGN PATENT DOCUMENTS 1476862  6/1977  United Kingdom ............. 514/241

OTHER PUBLICATIONS

F. C. Kull, et al., "Mixtures of Quaternary Ammonium Compounds and Long–chain Fatty Acids as Antifungal Agents", Applied Microbiology, 9: 538–541 (1961).

E. O. Bennett, Ph.D., "The Deterioration of Metal Cutting Fluids" Progress in Industrial Microbiology, 13: 121 (1974).

*Primary Examiner*—Allen J. Robinson
*Attorney, Agent, or Firm*—Finnegan, Henderson, Farabow, Garrett & Dunner

[57] ABSTRACT

Synergistic combinations of ionene polymers and hexahydro-1,3,5-tris(2-hydroxethyl)-s-triazine for use in controlling fungal and bacterial growth in synthetic metal working fluids.

1 Claim, No Drawings

SYNERGISTIC COMBINATIONS OF IONENES WITH HEXAHYDRO-1,3,5-TRIS-(2-HYDROXYETHYL)-S-TRIAZINE IN CONTROLLING FUNGAL AND BACTERIAL GROWTH IN SYNTHETIC METALWORKING FLUIDS

This application is a continuation of application Ser. No. 07/741,986, filed Aug. 6, 1991, now abandoned, which is a continuation of application Ser. No. 07/413,282, filed Sep. 27, 1989, now abandoned.

The invention is directed to synergistic antimicrobial combinations of ionene polymers with hexahydro-1,3,5-tris(2-hydroxyethyl)-s-triazine and their use in controlling fungal and/or bacterial growth in synthetic metalworking fluids.

BACKGROUND OF THE INVENTION

Ionene polymers, i.e., cationic polymers containing quaternary nitrogens in the polymer backbone, are known to be useful in controlling bacteria and algae in various aqueous systems. U.S. Pat. Nos. 3,874,870; 3,931,319; 4,027,020; 4,089,977; 4,506,081; 4,581,058; and 4,111,679 give various examples of these polymers. The disclosures of these patents are incorporated specifically by reference herein.

One such polymer is poly[oxyethylene(dimethyliminio)ethylene(dimethyliminio)ethylene dichloride]. This polymer is manufactured and sold by Buckman Laboratories Inc. under the names Busan ® 77 and WSCP ® as a biocide used primarily in aqueous systems, including concentrates of metalworking fluids for microorganism control.

Another such product is the ionene polymer produced by the condensation of equimolar amounts of dimethylamine and epichlorohydrin, as disclosed in U.S. Pat. No. 4,111,679.

Synergistic combinations of ionenes and hexahydro-1,3,5tris(2-hydroxyethyl)-s-triazine, however, do not appear to be known in the literature.

Both of these types of products are used alone to control microorganisms in industrial settings. Many industries experience problems caused by microorganisms. These problems are especially present where aqueous systems are used. The machining industry is one such industry in which problem-causing microorganisms are encountered. In machining operations, metalworking fluids are used primarily to reduce friction and heat, thereby reducing wear and prolonging the life of equipment.

Unfortunately, metalworking fluids have many properties which make them an ideal medium for the growth of bacteria and fungi. These microorganisms can cause such problems as: the buildup of slime/microbial deposits on machine surfaces, the clogging of jets and lines, the deterioration of the properties of the metalworking fluid itself, enhanced corrosion, as well as health and odor problems. Although bacteria are important in the biodeterioration of cutting fluids, fungi and yeast play an important role as well, especially in synthetic fluids. (Bennet, E. O., "The Deterioration of Metalworking Fluids", *Prog. Industrial Microbiology*, 13:121 (1974)).

As microorganisms grow in the metalworking fluid, the fluid begins to deteriorate and loses many of its essential properties. Its pH may drop and other chemical changes may occur until the fluid no longer is able to provide adequate lubrication. At this point, the fluid must be replaced with fresh fluid. This is costly and results in loss of production time.

The previously mentioned problems have resulted in the extensive use of biocides in metalworking fluid systems. Biocides may be incorporated in fluid concentrate or added to diluted fluids once they are in the holding tanks of the machine works.

There are many commercially available biocides used today. Each of these biocides is generally useful, but each is attended by a variety of impediments. Some biocides have odor problems, or create hazards with respect to storage, use or handling, which limit their utility. Presently, no one type of compound has significantly overcome any of the problems mentioned.

Economic factors should be considered before choosing a particular biocide for use in metalworking fluid systems. Such economic considerations apply to both the cost of the biocide and the expense of its application. The cost performance index of any biocide is derived from the basic cost of the material, its effectiveness per unit weight, the duration of its biocidal or biostatic effect in the system treated, and the ease and frequency of its addition to the system treated.

At present, none of the commercially available biocides is capable of exhibiting a prolonged biocidal effect. Instead, physical conditions, such as temperature and chemical reactivity with ingredients present in the system, often diminish or eliminate the effectiveness of the biocides. For example, many systems contain organic material which may react with a specific biocide or render it ineffective.

Hexahydro-1,3,5-tris(2-hydroxyethyl)-s-triazine has been used in the metalworking fluid industry for a long time. As can be seen in Table I, high concentrations of this compound are required to control both bacterial and fungal growth in metalworking fluids. One of the by-products of the hexahydro-1,3,5-tris(2-hydroxyethyl)-s-triazine is formaldehyde. Because of the carcinogenic properties of formaldehyde, it is desirable to use compounds that produce formaldehyde in the smallest quantities possible.

Metalworking fluid systems in which heavy microbial growth occurs would benefit from the practice of the present invention, which is described below. The practice of the present invention would also benefit many other systems, whether or not heavy microbial growth occurs, because it provides a more limited use of hexahydro-1,3,5-tris(2-hydroxyethyl)-s-triazine, a formaldehyde producing biocide.

SUMMARY OF THE INVENTION

The present invention controls fungal or bacterial growth in a synthetic metalworking fluid. The invention encompasses a composition comprising (a) hexahydro-1,3,5-tris(2-hydroxyethyl)-s-triazine and (b) an ionene polymer, wherein the ratio of component (a) to component (b) is from about 1:99 to about 99:1, and wherein the composition is formulated to synergistically control fungal or bacterial growth in a synthetic metalworking fluid.

The invention further relates to a method of controlling fungal or bacterial growth in a synthetic metalworking fluid comprising the step of adding to said metalworking fluid the composition defined above in an amount synergistically effective to control said fungal or bacterial growth.

The invention can be obtained by the simple addition of the two components (a) and (b) defined above, separately, to a concentrated synthetic metalworking fluid. In such case the invention encompasses a concentrated synthetic metalworking fluid comprising: a concentrated synthetic metalworking fluid containing components (a) and (b) as defined above, wherein the ratio of component (a) to component (b) is from about 1:99 to about 99:1, and wherein the amount of the components (a) and (b) is synergistically effective to control fungal or bacterial growth when said fluid is diluted and used at a metalworking site.

The method can also be practiced by separate addition of the components (a) and (b) to the diluted synthetic metalworking fluid at a metalworking site. Such separate administration of components (a) and (b) can be done simultaneously or sequentially.

An ionene polymer for the purposes of the present invention can be defined as a polymeric quaternary ammonium compound having the formula

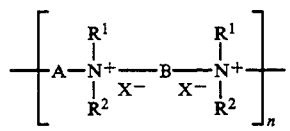

wherein X is a halogen and wherein $R^1$ and $R^2$, which can be the same or different, are selected from the group consisting of alkyl groups having from 1 to 20 carbon atoms and having either a 0 or 1 hydroxyl substituent, a benzyl group, and a benzene moiety bearing one alkyl group having from 2 to 20 carbon atoms; A and B can be the same or different and are selected from the group consisting of a divalent hydrocarbon radical containing 1 to 10 carbon atoms and which may contain one or more oxygen atoms either as an ether group, a hydroxy group, a carbonyl group or an amide group; n is a whole number from 1 to 15; and wherein the polymer may be capped on one or both ends with a quaternary ammonium group of the formula

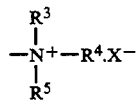

wherein X is defined as above and wherein $R^3$, $R^4$ and $R^5$, which can all be the same or different, are alkyl groups having from 1 to 20 carbon atoms and having either a 0 or 1 hydroxyl substituent, or $R^3$ and $R^4$ taken together with the nitrogen to which they are attached may form a saturated heterocyclic ring having from 5 to 7 ring atoms.

Substituents A and B may be substituted or unsubstituted. Preferably, A and B are substituted by at least one substituent selected from the group consisting of a hydroxyl group and a substituent substituted by at least one hydroxyl group.

Preferred substituents for both the A and B moieties, which can be identical or different, include $C_nH_{2n}OH$, wherein n ranges from 1 to 10, and more preferably $CH_2OH$, and also hydroxyaryl compounds, and most preferably hydroxyphenyl.

Hexahydro-1,3,5-tris(2-hydroxyethyl)-s-triazine can be easily prepared starting from formaldehyde and 2-hydroxyethanolamine. This compound is presently sold in varying concentrations in water with such commercial names as Grotan®, Busan® 1060, etc.

DETAILED DESCRIPTION OF THE INVENTION

When two chemical microbicides are combined into one product or added separately three things are possible:

1) The resulting product would produce an additive (neutral) effect
2) The chemicals in the product would produce an antagonistic effect, or
3) The chemicals in the product would produce a synergistic effect.

An additive effect has no economic advantage over the individual components. The antagonistic effect would produce a negative impact. Synergism would produce a positive value and therefore would be of economic advantage.

It is well known in the microbiocidal literature that there is no theoretical method to anticipate additive, antagonistic or synergistic effects when two biocides are mixed to yield a new formulation. Nor is there a way to predict the proportions of different biocides required to produce one of the three effects described above.

Hexahydro-1,3,5-tris(2-hydroxyethyl)-s-triazine is supplied either as a solid or a solution in water. One of the commercial formulations of this is Busan® 1060.

The ionene polymer may be chosen from a wide variety of known polymers based on compatibility of the ionene polymer with the metalworking fluid in use. Poly[oxyethylene(dimethyliminio)ethylene(dimethyliminio)ethylene dichloride] is known to be compatible with synthetic metalworking fluids.

One of the formulations of this polymer is supplied commercially as a 60% solution in water under the name Busan® 77. Another polymer, poly[2-hydroxypropylene(dimethyliminio) chloride] is formed by the condensation of epichlorohydrin and dimethylamine. This is supplied as a 60% solution in water.

In the following discussion, component (a) is hexahydro-1,3,5-tris-(2-hydroxyethyl)-s-triazine supplied as a 78.5% solution in water. Component (b) is an ionene polymer supplied as a 60% solution in water.

The ratio of component (a) to component (b) may range from 1:99 to about 99:1, preferably 20:80 to 80:20, more preferably 40:60 to 60:40, and most preferably 80:20.

The benefits of the invention are most evident in systems that are highly contaminated with microorganisms. These are systems with bacterial and fungal counts greater than $1.0 \times 10^6$/mL which are incapable of experiencing substantial count reduction when treated separately with low dosages of either an ionene polymer or hexahydro-1,3,5-tris(2-hydroxyethyl)-s-triazine. In these systems a low hexahydro-1,3,5-tris(2-hydroxyethyl)-s-triazine biocide or an ionene polymer fails to provide adequate preservation.

One of the unique features of this invention is that when hexahydro-1,3,5-tris(2-hydroxyethyl)-s-triazine, is used in conjunction with an ionene polymer, it is possible in many instances, to reduce the total fungal or bacterial count to zero cells per mL and maintain it at this level. When either of the biocides is used alone (at the same concentration as when used together), it fails to achieve and maintain a zero level of microbial growth.

The synergistic activity of the combinations described above has been confirmed using standard laboratory techniques as illustrated below.

The test method employed was the Standard Method for the Evaluation of Antimicrobial Agents in Aqueous Metalworking Fluids (ASTM Designation: E686-80).

The ASTM test is a multiple challenge test designed to simulate industrial conditions. A formulation containing both biocides is added to 450 mL aliquots of a synthetic metalworking fluid dilution. Controls contained only one of the biocides or no biocide. The metalworking fluid samples are then inoculated with 50 mL of a mixed, partially defined microbial culture and aerated on a specific time cycle. The cycle is composed of 5 days of aeration followed by two days without, which simulates an industrial work schedule. Every week, for a minimum of 6 weeks or until the test fails, the metalworking fluid samples are measured for microbial growth. This is done by enumerating the bacteria and fungi using standard plate-counting techniques.

The microorganisms used in the metalworking fluid inoculum included:
1) "Wild" fungi and bacteria obtained from a spoiled industrial fluid.
2) *Staphylococcus aureus*
3) *Pseudomonas aeruginosa*
4) *Klebsiella pneumoniae*
5) *Escherichia coli*

After six weeks a microbial count of 0 colony forming units (cfu) per mL was indicative of excellent preservation. This was also used as an endpoint for the synergism calculations.

Synergism was determined by the method of Kull, F. C., Euman, P. C., Sylwestrowicz, H. D., and Mayer, R. L., *Applied Microbiology* 9:538-541 (1961) using the ratio:

$$\frac{QA}{Qa} + \frac{QB}{Qb}$$

wherein
- Qa=Concentration of Compound A, in parts per million, acting alone, which produced an endpoint.
- Qb=Concentration of Compound B, in parts per million, acting alone, which produced an endpoint.
- QA=Concentration of Compound A, in parts per million, in the mixture, which produced an endpoint.
- QB=Concentration of Compound B, in parts per million, in the mixture, which produced an endpoint.

When the sum of QA/Qa+QB/Qb is greater than 1, antagonism is indicated, and when the sum is equal to 1, additivity is indicated. When the sum is less than one, synergism is demonstrated.

To disclose the nature of the present invention still more clearly, the following illustrative examples are given. It is to be understood, however, that the invention is not limited to the specific conditions or details set forth in the examples.

EXAMPLE 1

Synergistic combinations of hexahydro-1,3,5-tris(2-hydroxyethyl)-s-triazine and poly[oxyethylene(dimethyliminio)ethylene(dimethyliminio) ethylene dichloride]

Component (a) is a 78.5% solution of hexahydro-1,3,5-tris(2-hydroxyethyl)-s-triazine and component (b) is a 60% solution of poly[oxyethylene(dimethyliminio)ethylene(dimethyliminio)ethylene dichloride]. Components (a) and (b) are mixed in weight ratios of 80:20, 60:40, 40:60, and 20:80 and stirred for two hours to yield homogenous solutions. These solutions were added to metalworking fluids and tested according to the test methods described previously. The results are given in Table 1.

TABLE 1

Preservation Properties of Combinations of (a) Hexahydro-1,3,5-tris(2-hydroxyethyl)-s-triazine and (b) poly-[oxyethylene(dimethyliminio)ethylene(dimethyliminio)ethylene dichloride]

| Sample | Ratio of (a) to (b) | Component (a) (ppm) | Component (b) (ppm) | Bacteria/ mL (cfu) | Fungi/ mL (cfu) |
|---|---|---|---|---|---|
| 1 | — | 0 | 0 | $1.62 \times 10^7$ | $4.5 \times 10^7$ |
| 2 | 80:20 | 80 | 20 | $4.2 \times 10^6$ | $2.2 \times 10^6$ |
| 3 | " | 200 | 50 | 0 | 0 |
| 4 | 60:40 | 150 | 100 | $5.9 \times 10^5$ | $7.0 \times 10^4$ |
| 5 | " | 300 | 200 | 0 | 0 |
| 6 | 40:60 | 100 | 150 | $5.9 \times 10^5$ | $7.0 \times 10^4$ |
| 7 | " | 200 | 300 | 0 | 0 |
| 8 | 20:80 | 50 | 200 | $5.2 \times 10^6$ | $2.4 \times 10^5$ |
| 9 | " | 100 | 400 | 0 | 0 |
| 10 | — | 1500 | — | $1.4 \times 10^7$ | $9.8 \times 10^6$ |
| 11 | — | 3000 | — | 0 | 0 |
| 12 | — | — | 1000 | $4.6 \times 10^4$ | $2.1 \times 10^5$ |
| 13 | — | — | 3000 | 0 | 0 |

NOTE: Zero growth is used as a endpoint in the synergism calculations and indicates adequate preservation.

As can be seen from Table 1, combinations of component (a) and (b) are better in reducing bacterial and fungal counts in the metalworking fluids than either component (a) or (b) alone. In order to prove this synergism, calculations are made using the method described previously and the results are shown in Table 2.

TABLE 2

Synergism calculations for hexahydro-1,3,5-tris-(2-hydroxyethyl)-s-triazine with poly[oxyethylene(dimethyliminio)ethylene-(dimethyliminio)ethylene dichloride] in synthetic metalworking fluid for both bacteria and fungi

| Weight ratio of a to b | Quantities Producing End Points (ppm) | | | | | | |
|---|---|---|---|---|---|---|---|
| | Qa | QA | Qb | QB | $\frac{QA}{Qa}$ | $\frac{QB}{Qb}$ | $\frac{QA}{Qa} + \frac{QB}{Qb}$ |
| 100/0 | 3000 | — | — | — | — | — | — |
| 80/20 | — | 200 | — | 50 | .067 | .017 | .084 |
| 60/40 | — | 300 | — | 200 | .100 | .067 | .167 |
| 40/60 | — | 200 | — | 300 | .067 | .100 | .167 |
| 20/80 | — | 100 | — | 400 | .033 | .133 | .166 |
| 0/100 | — | — | 3000 | — | — | — | — |

As can be seen in Table 2, the sum of QA/Qa and QB/Qb is less than 1 which indicates synergism.

EXAMPLE 2

Synergistic combinations of hexahydro-1,3,5-tris (2-hydroxyethyl)-s-triazine and poly[2-hydroxypropylene-(dimethyliminio) chloride]

Component (a) is a 78.5% solution of hexahydro-1,3,5-tris(2-hydroxyethyl)-s-triazine and component (b) is a 60% solution of poly[2-hydroxypropylene-(dimethyliminio)chloride]. Component (a) and (b) are mixed in weight ratios of 80:20, 60:40, 40:60 and 20:80 and stirred for 2 hours to yield homogenous solutions. These solutions were added to metalworking fluids and tested according to the test methods described above. The results are listed in Table 3.

TABLE 3

Preservation Properties of Combinations of (a) Hexahydro-1,3,5-tris(2-hydroxyethyl)-s-triazine and (b) poly-[2-hydroxypropylene(dimethyliminio)chloride]

| Sample | Ratio of (a) to (b) | Component (a) (ppm) | Component (b) (ppm) | Bacteria/ mL (cfu) | Fungi/ mL (cfu) |
|---|---|---|---|---|---|
| 1 | — | 0 | 0 | $1.6 \times 10^7$ | $4.5 \times 10^7$ |
| 2 | 80:20 | 80 | 20 | $2.5 \times 10^6$ | $3.1 \times 10^6$ |
| 3 | " | 200 | 50 | 0 | 0 |
| 4 | 60:40 | 150 | 100 | $5.2 \times 10^5$ | $2.0 \times 10^6$ |
| 5 | " | 300 | 200 | 0 | 0 |
| 6 | 40:60 | 100 | 150 | $1.2 \times 10^6$ | $1.5 \times 10^6$ |
| 7 | " | 200 | 300 | 0 | 0 |
| 8 | 20:80 | 50 | 200 | $6.0 \times 10^5$ | $1.7 \times 10^6$ |
| 9 | " | 100 | 400 | 0 | 0 |
| 10 | — | 1500 | — | $1.4 \times 10^7$ | $9.8 \times 10^6$ |
| 11 | — | 3000 | — | 0 | 0 |
| 12 | — | — | 1500 | $5.1 \times 10^5$ | $1.2 \times 10^5$ |
| 13 | — | — | 2000 | 0 | 0 |

NOTE: Zero growth is used as an endpoint in the synergism calculations and indicates adequate preservation.

As can be seen from Table 3, combinations of components (a) (b) are better in reducing bacterial and fungal counts in metalworking fluids than either component (a) or (b) alone. In order to prove this synergism, calculations are made using the methods described above and the results are shown Table 4.

TABLE 4

Synergism calculations for hexahydro-1,3,5-tris-(2-hydroxyethyl)-s-triazine with poly[2-hydroxypropylene(dimethyliminio) chloride] in synthetic metalworking fluid for both bacteria and fungi

| Weight ratio of a to b | Qa | QA | Qb | QB | $\frac{QA}{Qa}$ | $\frac{QB}{Qb}$ | $\frac{QA}{Qa} + \frac{QB}{Qb}$ |
|---|---|---|---|---|---|---|---|
| 100/0 | 3000 | — | — | — | — | — | — |
| 80/20 | — | 200 | — | 50 | .067 | .025 | .092 |
| 60/40 | — | 300 | — | 200 | .100 | .100 | .200 |
| 40/60 | — | 200 | — | 300 | .067 | .150 | .217 |
| 20/80 | — | 100 | — | 400 | .033 | .200 | .233 |
| 0/100 | — | — | 200 | — | — | — | — |

As can be noted from Table 4, the sum of QA/Qa and QB/Qb is less than 1 which indicates synergism between the biocides.

The synergistic antifungal and antibacterial combinations described previously have synergistic activity when employed at appropriate concentrations and may be used to inhibit the growth of fungi and bacteria in metalworking fluids. It is obvious to those skilled in the art that the required synergistically effective amount (concentration) will vary depending on the particular organisms and particular applications, and can readily be determined by routine experimentation. Use of a synergistically effective amount enables the use of a substantially smaller amount of each of components (a) and (b) than would be necessary for each component if used alone, or than would be necessary if a mere additive effect from combining (a) and (b) were obtained.

In general, however, an effective fungicidal and bactericidal response will be obtained when the synergistic combination is employed in concentrations ranging from about 0.1 to about 5,000 ppm of hexahydro-1,3,5-tris(2-hydroxyethyl)-s-triazine, preferably 0.1 to 100 ppm, and from about 0.1 to about 10,000 ppm of ionene polymer, preferably 0.1 to 500 ppm.

What is claimed is:

1. A method of controlling fungal or bacterial growth in a synthetic metalworking fluid comprising the step of adding to said metalworking fluid a composition of hexahydro-1,3,5-tris(2-hydroxyethyl)-s-triazine and a polymeric quaternary ammonium ionene polymer in a synergistically effective amount to control said fungal or bacterial growth.

* * * * *